(12) United States Patent
Kumon et al.

(10) Patent No.: US 8,614,093 B2
(45) Date of Patent: Dec. 24, 2013

(54) PHARMACEUTICAL COMPOSITION FOR TREATING OR PREVENTING CANCER BY INDUCING DENDRITIC CELL-LIKE DIFFERENTIATION FROM MONOCYTES TO IMPROVE ANTICANCER IMMUNE ACTIVITY

(75) Inventors: Hiromi Kumon, Okayama (JP); Yasutomo Nasu, Okayama (JP); Masami Watanabe, Okayama (JP); Yuji Kashiwakura, Okayama (JP)

(73) Assignee: Momotaro-Gene Inc., Okayama-Shi, Okayama (JP)

( * ) Notice: Subject to any disclaimer, the term of this patent is extended or adjusted under 35 U.S.C. 154(b) by 340 days.

(21) Appl. No.: 12/934,394

(22) PCT Filed: Mar. 24, 2009

(86) PCT No.: PCT/JP2009/056428
§ 371 (c)(1),
(2), (4) Date: Apr. 19, 2011

(87) PCT Pub. No.: WO2009/119874
PCT Pub. Date: Oct. 1, 2009

(65) Prior Publication Data
US 2012/0034251 A1  Feb. 9, 2012

(30) Foreign Application Priority Data

Mar. 28, 2008  (JP) ................................. 2008-086516

(51) Int. Cl.
*C12N 5/00* (2006.01)
*C12N 5/02* (2006.01)
*C12N 5/071* (2010.01)

(52) U.S. Cl.
USPC .......................................... 435/377; 435/372

(58) Field of Classification Search
None
See application file for complete search history.

(56) References Cited

U.S. PATENT DOCUMENTS

| 2003/0068312 A1 | 4/2003 | McCarthy |
| 2008/0057540 A1 | 3/2008 | Bass et al. |
| 2009/0005538 A1 | 1/2009 | Kumon et al. |
| 2010/0173404 A1 | 7/2010 | Kumon et al. |
| 2011/0269824 A1 | 11/2011 | Kumon et al. |

FOREIGN PATENT DOCUMENTS

| EP | 2213309 A1 | 8/2010 |
| WO | 02/077204 A2 | 10/2002 |
| WO | W02006098074 A1 | 9/2006 |
| WO | 2007/064163 A1 | 6/2007 |
| WO | W02008050898 A1 | 5/2008 |
| WO | 2009/060982 A1 | 5/2009 |

OTHER PUBLICATIONS

Wang et al., 2001, J. Biol. Chem. vol. 276: 49213-220.*
Whisstock et al., 2003, Quart. Rev. Biophys. vol. 36: 307-340.*
Hsieh et al., "Dickkopf-3/REIC functions as a suppressor gene of tumor growth", Oncogene, vol. 23, 2004, pp. 9183-9189.
Watanabe et al., "Immunological aspects of REIC/Dkk-3 in monocyte differentiation and tumor regression", International Journal of Oncology, vol. 34, 2009, pp. 657-663.
Written Opinion dated Feb. 6, 2012, issued against Singapore Patent Application 201007072-0.
Search Report dated Feb. 6, 2012, corresponding with Singapore Patent Application 201007072-0.
Supplementary European Search Report corresponding with European Application 09725100.3 dated Dec. 21, 2011 (4 pages).
Masakiyo Sakaguchi et al., "Overexpression of REIC/Dkk-3 in Normal Fibroblasts Suppresses Tumor Growth via Induction of Interleukin-7", Journal of Biological Chemistry, vol. 284, No. 21, Mar. 11, 2009, pp. 14236-14244.
K. Kawasaki et al., "REIC/Dkk-3 overexpression downregulates P-glycoprotein in multidrug-resistant MCF7/ADR cells and induces apoptosis in breast cancer", Cancer Gene Therapy, vol. 16, No. 1, Jul. 25, 2008, pp. 65-72.
International Search Report corresponding with International Application No. PCT/JP2009/056428 dated Apr. 21, 2009, 1 page.
Fernando Abarzua, "Fundamental Experiment on Gene Therapy for Human Prostate Cancer Using REIC/DKK-3 Gene", Journal of Okayama Medical Association, vol. 119, May 2007, pp. 21-26.
K. Edamura et al., "Adenovirus-mediated REIC/Dkk-3 gene transfer inhibits tumor growth and metastasis in an orthotopic prostate cancer model", Cancer Gene Therapy, 2007, vol. 14, pp. 765-772.
Ryuta Tanimoto et al., "REIC/Dkk-3 as a potential gene therapeutic agent against human testicular cancer", International Journal of Molecular Medicine, vol. 19, 2007, pp. 363-368.
Haruki Kaku et al., "Basic research study on prostate cancer gene therapy and approach toward translational research (TR)", Nishinihom J. Urology, vol. 69, 2007 pp. 221-229 (partial translation).
Fernando Abarzua et al., "Adenovirus-Mediated Overexpression of REIC/Dkk-3 Selectively Induces Apoptosis in Human Prostate Cancer Cells through Activation of c-Jun NH2-Kinase", (www.aacrjournals,org), Cancer Research 2005, vol. 65:(21), Nov. 1, 2005, pp. 9617-9622.
Fernando Abarzua et al., "An N-terminal 78 amino acid truncation of REIC/Dkk-3 effectively induces apoptosis", Elsevier, Biochemical and Biophysical Research Communications, vol. 375, 2008, pp. 614-618.

* cited by examiner

*Primary Examiner* — Amy Juedes
(74) *Attorney, Agent, or Firm* — Fitch, Even, Tabin & Flannery LLP

(57) ABSTRACT

According to the present invention, a composition for inducing or activating dendritic cell-like cells so as to treat or prevent cancer by immunotherapy is provided.
Specifically, the following is provided: an agent for activating cancer immunity, which comprises, as an active ingredient, the following REIC protein:
(a) a protein consisting of the amino acid sequence shown in SEQ ID NO: 2; or
(b) a protein consisting of an amino acid sequence derived from the amino acid sequence shown in SEQ ID NO: 2 by substitution, deletion, or addition of one or more amino acid(s) and having the activity of inducing differentiation from monocytes into dendritic cell-like cells.

4 Claims, 14 Drawing Sheets

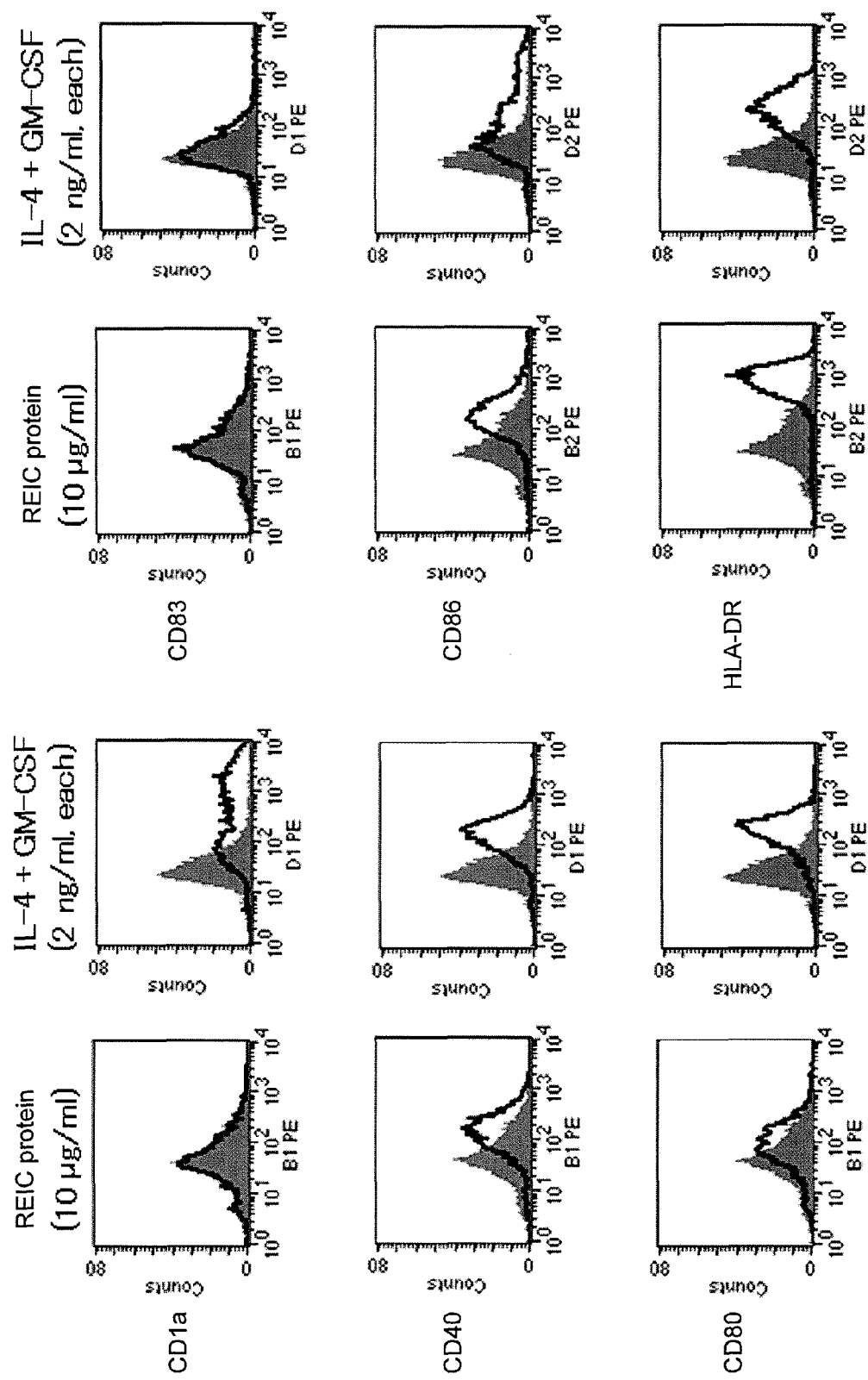

PHARMACEUTICAL COMPOSITION FOR TREATING OR PREVENTING CANCER BY INDUCING DENDRITIC CELL-LIKE DIFFERENTIATION FROM MONOCYTES TO IMPROVE ANTICANCER IMMUNE ACTIVITY

CROSS-REFERENCE TO RELATED APPLICATIONS

This is the U.S. National Phase of International Application PCT/JP2009/056428, filed Mar. 24, 2009, and claims priority benefit under 35 U.S.C. §119 based on Japanese Application No. 2008-086516, filed Mar. 28, 2008, the entire disclosures of which applications are hereby incorporated herein by reference.

TECHNICAL FIELD

The present invention relates to a pharmaceutical composition for treating or preventing cancer by improving anticancer immune activity.

BACKGROUND ART

Dendritic cells (DCs) are the most powerful antigen presenting cells in the living body. Dendritic cells are known to induce immune responses by presenting antibodies to T cells. In addition, it is also known that DCs play a central role in immune reactions by directly acting not only on T cells but also on B cells, NK cells, NKT cells, and the like. Immature DCs receive antigen stimulation so as to cause an increase in the expression of CD40, CD80, CD86, or the like. Accordingly, DCs attain T cell stimulatory capacity. In addition, DCs migrate to peripheral lymphatic tissue and activate T cells that are specific to antigens incorporated thereinto so as to induce immune responses.

In general, there are only a small number of references that disclose substances recognized as having the ability to induce dendritic cell(-like) differentiation from blood precursor cells. Most such substances are well-known cytokines. For instance, there are many reports on the induction of differentiation caused by the combined use of GM-CSF and IL-4. This combination is called a "gold standard" for dendritic cell differentiation. In addition, as substances capable of inducing dendritic cell differentiation when used alone or in combination, TNF-alpha, IL-2, IL-3, IL-6, IL-7, IL-12, IL-13, IL-15, HGF (hepatocyte growth factor), a CD40 ligand, M-CSF, an Flt3 ligand, and TGF-beta have been reported. Among these proteins, examples of a substance capable of inducing precursor cells to differentiate into dendritic cell(-like) cells when used alone include IL-2, IL-15, HGF, and a CD40 ligand. Of these, only IL-2 has been confirmed to have in vivo anticancer effects (see Non-Patent Document 1).

Meanwhile, the REIC gene is known as a gene involved in cell immortalization. It has been reported that the expression of the gene is suppressed in cancer cells (see Patent Document 1 and Non-Patent Documents 2 to 5).

The REIC gene is a member of the Dkk family. It has been suggested that Dkk-1, which is a member of such family, inhibits Wnt signal transduction via Wnt receptors (Non-Patent Documents 6 and 7). The Wnt gene has been reported to play multifaceted roles in important biological phenomena such as cell growth, cell differentiation, and canceration (see Non-Patent Document 8). Therefore, similarly, the Dkk family (including 4 currently known human genes) probably has important functions for cell growth, cell differentiation, and canceration. However, most of the functions of the Dkk family have not been elucidated.

Patent Document 1: WO01/038523
Non-Patent Document 1: Zou G M. Et al., Eur Cytokine Netw. 2002 April-June; 13(2):186-99.
Non-Patent Document 2: Tsuji, T. et al., BiochemBiophys Res Commun 268, 20-4 (2000)
Non-Patent Document 3: Tsuji, T. et al., BiochemBiophys Res Commun 289, 257-63 (2001)
Non-Patent Document 4: Nozaki, I. et al., Int J Oncol 19, 117-21 (2001)
Non-Patent Document 5: Kurose, K. et al., J Urol 171, 1314-8 (2004)
Non-Patent Document 6: Bafico, A. et al., Nat Cell Biol 3, 683-6 (2001)
Non-Patent Document 7: Hoang, B. H. et al., Cancer Res 64, 2734-9 (2004)
Non-Patent Document 8: Moon, R. T. et al., Science 296, 1644-6 (2002)

DISCLOSURE OF THE INVENTION

It is an object of the present invention to induce or activate dendritic cell-like cells so as to treat or prevent cancer by immunotherapy.

As described above, the IL-2 protein, which is an immunological cancer therapeutic agent, exhibits therapeutic effects upon specific types of cancer such as renal cell cancer in some cases. However, it is well-known in clinical practice that the types of cancer for which the protein can be administered and the effects of such protein are limited.

The present inventors conducted intensive studies on the cancer immunotherapeutic effects of the REIC(REIC/Dkk-3) protein that had been previously isolated by the present inventors. As a result, the present inventors found that the REIC protein can induce monocytes to differentiate into dendritic cell-like cells, allowing the dendritic cell-like cells to cause an immune reaction against a cancer antigen, and thus allowing treatment or prevention of cancer. This has led to the completion of the present invention, which relates to the use of the REIC protein as a dendritic cell differentiation-inducing agent, an agent for activating cancer immunity, or a cancer therapeutic or prophylactic agent. The present inventors found that the REIC protein, which is found to be expressed/secreted at a decreased level in almost any type of cancer, can be used as a cancer therapeutic agent having the effect of activating cancer immunity against various types of cancer, and that the therapeutic effects of the REIC protein may be superior to the therapeutic effects of IL-2. The present inventors have demonstrated that the REIC protein itself can induce anticancer immunity, and they have confirmed the usefulness of the REIC protein for in vivo immune and inflammation phenomena. In view of carcinogenesis, the REIC protein concentration is probably low in tissue in which canceration progresses (because the expression or secretion of the REIC protein is absent or reduced in many types of cancer cells). Therefore, it is thought that the anticancer immune activity is unlikely to be induced in cancer tissue so that the presence of cancer is not detected through the biological immunity (cancer cell immunological tolerance), resulting in proliferation or progression of cancer. Under such circumstances, the REIC protein is also useful as an agent for preventing canceration/carcinogenesis through anticancer immune activation.

Specifically, the present invention is described as follows.

[1] An agent for inducing differentiation from monocytes into dendritic cell-like cells, which comprises, as an active ingredient, the following REIC protein:
(a) a protein consisting of the amino acid sequence shown in SEQ ID NO: 2; or
(b) a protein consisting of an amino acid sequence derived from the amino acid sequence shown in SEQ ID NO: 2 by substitution, deletion, or addition of one or more amino acid(s) and having the activity of inducing differentiation from monocytes into dendritic cell-like cells.

[2] The agent for inducing differentiation from monocytes into dendritic cell-like cells according to [1], wherein the monocytes are peripheral blood monocytes.

[3] An agent for activating cancer immunity, which comprises, as an active ingredient, the following REIC protein:
(a) a protein consisting of the amino acid sequence shown in SEQ ID NO: 2; or
(b) a protein consisting of an amino acid sequence derived from the amino acid sequence shown in SEQ ID NO: 2 by substitution, deletion, or addition of one or more amino acid(s) and having the activity of inducing differentiation from monocytes into dendritic cell-like cells.

[4] The agent for activating cancer immunity according to [3], wherein the monocytes are peripheral blood monocytes.

[5] A pharmaceutical composition for cancer therapy or prevention having the effect of activating cancer immunity, which comprises the agent for activating cancer immunity according to [3] or [4].

[6] An agent for inducing differentiation from monocytes into dendritic cell-like cells, which comprises, as an active ingredient, the following REIC DNA:
(a) DNA consisting of the nucleotide sequence shown in SEQ ID NO: 1; or
(b) DNA that hybridizes under stringent conditions to DNA consisting of a nucleotide sequence complementary to the nucleotide sequence shown in SEQ ID NO: 1 and encodes a protein having the activity of inducing differentiation from monocytes into dendritic cell-like cells.

[7] The agent for inducing differentiation from monocytes into dendritic cell-like cells according to [6], wherein the monocytes are peripheral blood monocytes.

[8] An agent for activating cancer immunity, which comprises, as an active ingredient, the following REIC DNA:
(a) DNA consisting of the nucleotide sequence shown in SEQ ID NO: 1; or
(b) DNA that hybridizes under stringent conditions to DNA consisting of a nucleotide sequence complementary to the nucleotide sequence shown in SEQ ID NO: 1 and encodes a protein having the activity of inducing differentiation from monocytes into dendritic cell-like cells.

[9] The agent for activating cancer immunity according to [8], wherein the monocytes are peripheral blood monocytes.

[10] A pharmaceutical composition for cancer therapy or prevention having the effect of activating cancer immunity, which comprises the agent for activating cancer immunity according to [8] or [9].

[11] An agent for inducing differentiation from monocytes into dendritic cell-like cells, which comprises, as an active ingredient, a vector containing the following REIC DNA:
(a) DNA consisting of the nucleotide sequence shown in SEQ ID NO: 1; or
(b) DNA that hybridizes under stringent conditions to DNA consisting of a nucleotide sequence complementary to the nucleotide sequence shown in SEQ ID NO: 1 and encodes a protein having the activity of inducing differentiation from monocytes into dendritic cells or dendritic cell-like cells.

[12] The agent for inducing differentiation from monocytes into dendritic cell-like cells according to [11], wherein the vector is an adenovirus vector.

[13] The agent for inducing differentiation from monocytes into dendritic cell-like cells according to [11] or [12], wherein the monocytes are peripheral blood monocytes.

[14] An agent for activating cancer immunity comprising, as an active ingredient, a vector containing the following REIC DNA:
(a) DNA consisting of the nucleotide sequence shown in SEQ ID NO: 1; or
(b) DNA that hybridizes under stringent conditions to DNA consisting of a nucleotide sequence complementary to the nucleotide sequence shown in SEQ ID NO: 1 and encodes a protein having the activity of inducing differentiation from monocytes into dendritic cells or dendritic cell-like cells.

[15] The agent for activating cancer immunity according to [14], wherein the monocytes are peripheral blood monocytes.

[16] The agent for activating cancer immunity according to [14] or [15], wherein the vector is an adenovirus vector.

[17] A pharmaceutical composition for cancer therapy or prevention having the effect of activating cancer immunity, which comprises the agent for activating cancer immunity according to any one of [14] to [16].

[18] The pharmaceutical composition for cancer therapy or prevention having the effect of activating cancer immunity according to [17], wherein the vector is an adenovirus vector.

[19] A method for inducing CD14 positive monocytes to differentiate into dendritic cell-like cells, which comprises culturing monocytes collected from an animal in vitro in the presence of the following REIC protein:
(a) a protein consisting of the amino acid sequence shown in SEQ ID NO: 2; or
(b) a protein consisting of an amino acid sequence derived from the amino acid sequence shown in SEQ ID NO: 2 by substitution, deletion, or addition of one or more amino acid(s) and having the activity of inducing differentiation from monocytes into dendritic cell-like cells.

[20] The method according to [19], wherein the monocytes are peripheral blood monocytes.

[21] Dendritic cell-like differentiated cells, which have been induced to differentiate from monocytes activated by the REIC protein by the method according to [19] or [20].

[22] The dendritic cell-like differentiated cells according to [21], which are positive for CD11c, CD40, CD80, CD86, HLA-DR, and CD14 and negative for CD1a.

[23] The dendritic cell-like differentiated cells according to [21], which are found to express almost no CD1a but express CD14 at a level greater than that expressed in dendritic cells that have been induced from monocytes with the use of GM-CSF and IL-4 when antigens on the cell surfaces are analyzed by flow cytometry.

This description includes part or all of the contents as disclosed in the description and/or drawings of Japanese Patent Application No. 2008-086516, which is a priority document of the present application.

BRIEF DESCRIPTION OF DRAWINGS

FIG. 6B shows the results of flow cytometry analysis of dendritic cell-like cells induced to differentiate with the addition of the human REIC protein.

BEST MODES FOR CARRYING OUT THE INVENTION

Figure 1:
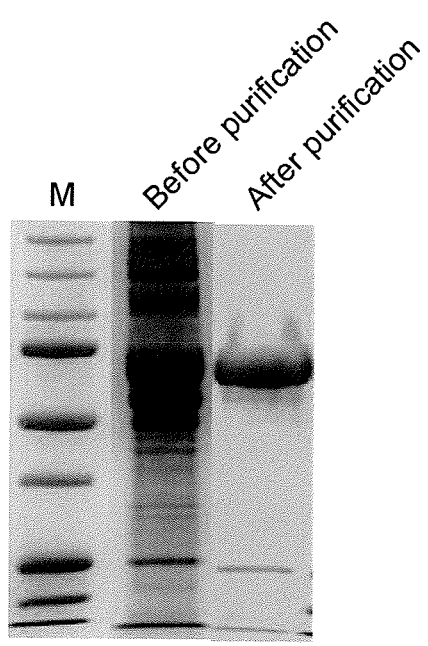
FIG. 1 shows an image indicating the results of western blot analysis of the purified human REIC protein.

Hereafter, the present invention is described in detail.

The agent for inducing differentiation from monocytes into dendritic cell-like cells, the agent for activating cancer immunity, and the pharmaceutical composition for cancer therapy or prevention having the effect of activating cancer immunity of the present invention comprise, as an active ingredient, REIC DNA or the REIC protein encoded by such DNA.

The nucleotide sequence of REIC DNA is shown in SEQ ID NO: 1. In addition, the amino acid sequence of the REIC protein encoded by REIC DNA is shown in SEQ ID NO: 2.

A protein encoded by REIC DNA contained in the agent for inducing differentiation from monocytes into dendritic cell-like cells, the agent for activating cancer immunity, and the pharmaceutical composition for cancer therapy or prevention having the effect of activating cancer immunity of the present invention is a protein comprising the amino acid sequence shown in SEQ ID NO: 2 or an amino acid sequence substantially identical to the amino acid sequence shown in SEQ ID NO: 2 and having the activity of inducing differentiation from monocytes into dendritic cell-like cells. Herein, such substantially identical amino acid sequence includes an amino acid sequence derived from the above amino acid sequence by substitution, deletion and/or addition of one or more (1 to 10, preferably 1 to 5, and more preferably 1 or 2) amino acid(s) or an amino acid sequence having at least 85%, preferably 90% or higher, further preferably 95% or higher, and particularly preferably 97% or higher identity to the above amino acid sequence, which is calculated using, for example, BLAST (Basic Local Alignment Search Tool) at the National Center for Biological Information (with the use of, for example, default (i.e., initial) parameters).

A protein encoded by REIC DNA can be obtained by chemical synthesis based on the sequence information of SEQ ID NO: 1 or SEQ ID NO: 2. In addition, it can be obtained in the form of a recombinant REIC protein by a gene engineering technique. Further, it can also be obtained according to the descriptions in WO01/038523.

REIC DNA contained in the agent for inducing differentiation from monocytes into dendritic cell-like cells, the agent for activating cancer immunity, and the pharmaceutical composition for cancer therapy or prevention having the effect of activating cancer immunity of the present invention is DNA that encodes a protein having the activity of inducing differentiation from monocytes into dendritic cell-like cells. Such DNA is selected from among the following examples: DNA that hybridizes under stringent conditions to DNA having a nucleotide sequence complementary to the nucleotide sequence shown in SEQ ID NO: 1; DNA having at least 85% or higher, preferably 90% or higher, more preferably 95% or higher, and particularly preferably 97% or higher identity to the nucleotide sequence shown in SEQ ID NO: 1, which is calculated using, for example, BLAST (Basic Local Alignment Search Tool) at the National Center for Biological Information (with the use of, for example, default (i.e., initial) parameters); and DNA that encodes a protein comprising an amino acid sequence derived from the amino acid sequence of the protein encoded by the aforementioned DNA by substitution, deletion and/or addition of one or more (1 to 10, preferably 1 to 5, and more preferably 1 or 2) amino acid(s). Under "stringent conditions" referred to herein, for example, hybridization is carried out with 1×SSC, 0.1% SDS, and 37° C. Under more stringent conditions, it is carried out with 0.5×SSC, 0.1% SDS, and 42° C. Under further stringent conditions, it is carried out with 0.2×SSC, 0.1% SDS, and 65° C. Further, REIC DNA contained in the agent for inducing differentiation from monocytes into dendritic cell-like cells, the agent for activating cancer immunity, and the pharmaceutical composition for cancer therapy or prevention having the effect of activating cancer immunity of the present invention is DNA that encodes the protein shown in SEQ ID NO: 2.

The expression "activity of inducing differentiation from monocytes into dendritic cell-like cells" used herein refers to activity that causes monocytes to differentiate into dendritic cell-like cells. It is possible to detect whether or not the addition of the REIC protein results in the induction of differentiation into dendritic cell-like cells based on morphological characteristics and the presence of surface antigens. Specifically, such dendritic cell-like cells are morphologically characterized by their dendrites. Also, such dendritic cell-like cells are characterized in that they are found to be positive for dendritic cell markers such as CD11c, CD40, CD80, CD86, and HLA-DR, which are surface antigens, by flow cytometry analysis.

REIC DNA can be obtained from human cells, human tissues, or the like based on the sequence information of SEQ ID NO: 1. In addition, it can be obtained in accordance with the descriptions in WO01/038523.

Further, the present invention includes a vector comprising REIC DNA. The vector may be introduced into a subject in order to express the REIC protein in the body of the subject and exhibit the effects of inducing differentiation from monocytes into dendritic cell-like cells, effects of activating cancer immunity, and effects of treating or preventing cancer based on the effects of activating cancer immunity.

In gene therapy, a target gene (DNA) can be introduced into a subject in accordance with a conventional technique. Examples of techniques for introducing a gene into a subject include a method involving the use of a virus vector and a method involving the use of a non-virus vector. Various techniques are known (*Bessatsu Jikken-Igaku* (*Separate volume, Experimental Medicine*), *Idenshi-Chiryo-No-Kisogijutsu* (*Basic Techniques for Gene Therapy*), Yodosha Co., Ltd., 1996; *Bessatsu Jikken Igaku* (*Separate volume, Experimental Medicine*), *Idenshi donyu & hatsugen kaiseki jikken-hou* (*Experimentation of gene introduction & expression analysis*), Yodosha, Co., Ltd., 1997; and the Japan Society of Gene Therapy (ed.), "*Idenshi chiryo kaihatsu kenkyu handbook* (*the Handbook for research and development of gene therapy*)," N.T.S., 1999).

Representative examples of virus vectors used for gene introduction include an adenovirus vector, an adeno-associated virus vector, and a retrovirus vector. A target gene may be introduced into a cell by introducing a target gene into a DNA or RNA virus, such as a detoxicated retrovirus, herpes virus, vaccinia virus, poxvirus, poliovirus, Sindbis virus, Sendai virus, SV40, or human immunodeficiency virus (HIV), and infecting the cell with such recombinant virus.

When the gene of the present invention is used for gene therapy using a virus, an adenovirus vector is preferably used. An adenovirus vector is characterized in that: (1) it can introduce genes into multiple types of cells; (2) it can efficiently introduce genes into cells at the period of growth arrest; (3) it enables concentration via centrifugation to yield high-titer viruses (10 to 11 PFU/ml or more); and (4) it is suitable for direct gene introduction into tissue cells in vivo. As adenovirus vectors used for gene therapy, the second-generation adenovirus vector prepared from the first-generation adenovirus vector lacking the E1/E3 region (Miyake, S. et al., Proc. Natl. Acad. Sci., U.S.A., 93, 1320, 1996) by deleting the E2 or E4 region in addition to the E1/E3 region (Lieber, A. et al., J. Virol., 70, 8944, 1996; Mizuguchi, H. & Kay, M. A., Hum. Gene Ther., 10, 2013, 1999) and the third-generation adenovirus vector lacking substantially all the adenovirus genome (GUTLESS) (Steinwaerder, D. S., et al., J. Virol., 73, 9303, 1999) have been developed. The gene of the present invention can be introduced with the use of any of such adenovirus vectors without particular limitation. Further, the adeno-AAV hybrid vector to which the capacity for incorporating the gene into the AAV chromosome has been imparted (Recchia, A. et al., Proc. Natl. Acad. Sci., U.S.A., 96, 2615, 1999) or an adenovirus vector capable of incorporating the gene into the chromosome with the use of a transposon gene may be used, so that such vector can be applied to long-term gene expression. Also, a peptide sequence exhibiting tissue-specific transferability to the H1 loop of the adenovirus fiber may be inserted to impart tissue specificity to the adenovirus vector (Mizuguchi, H. & Hayakawa, T., Nippon Rinsho, 7, 1544, 2000).

According to the present invention, an adenovirus vector comprising REIC DNA is called "Ad-REIC."

Alternatively, the target gene can be introduced into a cell or tissue using a recombinant expression vector into which a gene expression vector, such as a plasmid vector, has been incorporated, without the use of the above viruses. For example, a gene can be introduced into a cell via lipofection, calcium phosphate coprecipitation, a DEAE-dextran method, or direct injection of DNA using a micro glass tube. Also, a recombinant expression vector can be incorporated into a cell via, for example, gene introduction using an internal liposome, gene introduction using an electrostatic type liposome, a method using HVJ-liposome, a method using a modified HVJ-liposome (i.e., the HVJ-AVE liposome method), a method using an HVJ-E (envelope) vector, receptor-mediated gene introduction, a method in which a particle gun is used to introduce DNA molecules in a cell with a carrier (i.e., a metal particle), direct introduction of naked-DNA, or gene introduction using various types of polymers. In such a case, any expression vector can be used, provided that such vector can express the target gene in vivo. Examples of such vectors include expression vectors such as pCAGGS (Gene 108, 193-200, 1991), pBK-CMV, pcDNA3.1, and pZeoSV (Invitrogen, Stratagene), and pVAX1 vectors.

A vector comprising REIC DNA may adequately comprise a promoter or enhancer for transcribing the gene, poly A signal, a marker gene for labeling and/or selecting the cell into which the gene has been introduced, and the like. In such a case, a known promoter can be used.

The vector comprising REIC DNA of the present invention may be introduced into a subject by, for example, the in vivo method wherein a gene therapeutic agent is directly introduced into the body or the ex vivo method wherein a given cell is extracted from a human, a gene therapeutic agent is introduced into the cell ex vivo, and the cell is then returned into the body (*Nikkei Science*, April 1994, pp. 20-45; *Gekkan Yakuji*, 36(1), 23-48, 1994; *Jikken igaku zoukan* (*Extra volume, Experimental Medicine*), 12(15), 1994; the Japan Society of Gene Therapy (ed.), *Idenshi chiryo kaihatsu kenkyu handbook*, N. T. S., 1999).

Monocytes used in the present invention include peripheral blood-derived monocytes, bone marrow-derived monocytes, splenocyte-derived monocytes, and umbilical cord blood-derived monocytes. Of these, peripheral blood-derived monocytes are preferable. When specific monocytes such as CD14 positive monocytes are collected from a living body and induced by the REIC protein to differentiate into dendritic cell-like cells, such monocytes can be collected by an FACS (fluorescent activated cell sorter), a flow cytometer, or the like with the use of the presence of CD14 as an index. The animal species that is the origin of monocytes is not limited. Examples of animals that can be used include mammals such as mice, rats, guinea pigs, hamsters, rabbits, cats, dogs, sheep, pigs, bovines, horses, goats, monkeys, and humans. Isolation of a specific cell population by an FACS can be carried out by a known method. As an FACS or a flow cytometer, an FACS vantage (Becton, Dickinson and Company), an FACS Calibur (Becton, Dickinson and Company), or the like can be used.

Monocytes can be cultured by a known technique for culturing human lymphoid cells. For a culture solution, for example, a known base medium such as RPMI1640 or DMEM can be used. Culture may be carried out by adding an appropriate antibiotic, animal serum, or the like to such base medium. Culture vessels used herein are not limited. Commercially available plates, dishes, and flasks can be selected and used depending on the culture scale.

The present invention includes a method for culturing monocytes in vitro in the presence of the REIC protein and inducing differentiation from monocytes into dendritic cell-like cells. In the method of the present invention, for example, culture may be carried out using monocytes at a concentration of $10^4$ to $10^7$ cells/ml with the addition of the REIC protein at a concentration of 1 to 20 µg/ml.

Dendritic cells play a very important role in the mechanisms of cancer immunity, inflammation, and the like in the living body. Dendritic cell-like cells induced to differentiate by the REIC protein according to the method of the present invention are morphologically similar to dendritic cells induced by IL-4+GM-CSF. However, to be exact, the dendritic cell-like cells differ from such dendritic cells, and therefore they are novel dendritic cell-like cells. Dendritic cell-like cells induced by the REIC protein are in dendritic forms. In addition, the dendritic cell-like cells are positive for dendritic cell markers such as CD11c, CD40, CD80, CD86, and HLA-DR. In this regard, novel dendritic cell-like cells of the present invention can be classified as dendritic cells. However, they are negative for CD1a, which is a dendritic cell marker, and positive for CD14, for which dendritic cells are generally supposed to be negative.

In the case of induction from CD14 positive monocytes with stimulation with the REIC protein, it refers to "dendritic cell-like differentiated cells that have been activated by the REIC protein (REIC activated monocytes with dendritic cell features)."

The present invention encompasses dendritic cell-like cells induced from CD14 positive monocytes by the REIC protein. Dendritic cell-like cells obtained via induction by the REIC protein can be used for cancer immunotherapy. Specifically, monocytes are collected from a subject, the monocytes are cultured with the REIC protein, the dendritic cell-like cells are induced, and then the obtained dendritic cell-like cells are returned to the subject. Thus, dendritic cell-like cells themselves can be used for cancer therapy or prevention, or the like. In such case, the REIC protein-induced dendritic cell-like cells act in a non-cancer-type-specific manner and exert cancer immunotherapeutic effects. However, it is also possible to add a cancer-type specific tumor antigen upon induction of dendritic cell-like cells. In addition, induced dendritic cell-like cells can be cocultured with a specific tumor antigen. It becomes possible to attack cancer cells in a tumor-specific manner by stimulating dendritic cell-like cells with a cancer-type-specific tumor antigen. In addition, the REIC protein-induced dendritic cell-like cells of the present invention have the ability to cause $CD4^+$ T cells to proliferate, allowing the enhancement of anticancer immune activity for a subject.

Dendritic cell-like cells can be intradermally, subcutaneously, intravenously, or intralymphaticaly administered.

In addition, the REIC protein is thought to have a cytokine-like activity such that the protein acts on cells in an extracellular manner so as to control cell differentiation. Therefore, it is believed that the REIC protein widely functions in vivo in relation to immunity and inflammation. Thus, the REIC protein or DNA encoding the same can be administered to a subject as an agent for inducing differentiation into dendritic cell-like cells or an agent for activating dendritic cell-like cells for in vivo use. The REIC protein induces dendritic cell-like cells in a subject. As a result, the dendritic cell-like cells systematically activate lymphocytes having anticancer activity in the subject, resulting in the exhibition of cancer immune effects. Therefore, the REIC protein or DNA encoding the same can be used as an agent for activating cancer immunity. Further, since the REIC protein-induced dendritic cell-like cells have cancer immune effects, the REIC protein or DNA encoding the same can be used as a pharmaceutical composition for cancer therapy or prevention (a cancer immunotherapeutic agent). In such case, the REIC protein or DNA encoding the same may be administered alone. In this case, the effects are exhibited in a non-cancer-type-specific manner. Alternatively, it may be administered with a specific tumor antigen. In such a case, the effects can be exhibited in a cancer-type-specific manner.

Examples of a cancer that is treated or prevented according to the present invention include cranial nerve tumor, skin cancer, gastric cancer, lung cancer, hepatic cancer, lymphoma/leukemia, colon cancer, pancreatic cancer, anal/rectal cancer, esophageal cancer, uterine cancer, breast cancer, adrenal cancer, kidney cancer, renal pelvic and ureteral cancer, bladder cancer, prostate cancer, urethral cancer, penile cancer, testicular cancer, osteoma/osteosarcoma, leiomyoma, rhabdomyoma, and mesoepithelioma. In particular, breast cancer and bladder cancer are preferable.

The agent for inducing differentiation from monocytes into dendritic cell-like cells, the agent for activating cancer immunity, and the pharmaceutical composition for cancer therapy or prevention having the effect of activating cancer immunity of the present invention comprises REIC DNA, a vector comprising the DNA, or protein encoded by the DNA, and a pharmacologically acceptable carrier, diluent, or excipient.

The agent for inducing differentiation from monocytes into dendritic cell-like cells, the agent for activating cancer immunity, and the pharmaceutical composition for cancer therapy or prevention having the effect of activating cancer immunity of the present invention can be administered in a variety of dosage forms. Examples of dosage forms include: oral administration, such as a tablet, capsule, granule, powder, and syrup; and parenteral administration, such as injection, drop, suppository, spray, eye drop, nasal agent, and patch.

The agent for inducing differentiation from monocytes into dendritic cell-like cells, the agent for activating cancer immunity, and the pharmaceutical composition for cancer therapy or prevention having the effect of activating cancer immunity of the present invention can be topically administered. For example, the composition can be administered to a site of cancer via injection to provide the effects thereof.

Preferably, the agent of the present invention is injected into a localized cancer region once or two or more times or it is directly injected into the entire cancer lesion so as to spread therein.

The agent for inducing differentiation from monocytes into dendritic cell-like cells, the agent for activating cancer immunity, and the pharmaceutical composition for cancer therapy or prevention having the effect of activating cancer immunity of the present invention comprises a carrier, a diluent, and an excipient that are generally used in the drug manufacturing field. For example, lactose or magnesium stearate can be used as a carrier or excipient of a tablet. Physiological saline, a glucose solution, or an isotonic solution containing another adjuvant is used as an aqueous solution of an injection. Such solution may be used in combination with an adequate solubilizer, such as alcohol, a polyalcohol such as propylene glycol, or a nonionic surfactant. Sesame oil, soybean oil, or the like is used as an oily liquid, and, as a solubilizer, benzyl benzoate, benzyl alcohol, or the like may be used in combination.

The dose varies depending on symptoms, age, body weight, and other conditions. A dose of 0.001 mg to 100 mg may be administered at intervals of several days, several weeks, or several months via hypodermic injection, intramuscular injection, or intravenous injection.

The present invention is hereafter described in detail with reference to the following examples, although the present invention is not limited thereto.

Preparation of Recombinant Human REIC Protein

A recombinant human REIC protein was prepared in the manner described below.

1. A plasmid encoding the full-length human REIC gene was introduced into CHO cells via electroporation. Thus, clones capable of stably expressing human REIC were established. The cells ($10^7$ cells in total) were cultured in a protein-free medium (C5467, Sigma) containing 2 mM L-glutamine and 8 μM puromycin at 37° C. in the presence of 5% $CO_2$ for 1 week during moderate shaking. A CHO cell culture was collected by centrifugation at 2,000 rpm for 5 minutes. Then, the supernatant was obtained (1 L).
2. The supernatant was centrifuged at 4° C. at 15000 rpm for 40 minutes.
3. The thus obtained supernatant was filtrated using a 0.22 μm filter (TP099505, TPP, Trasadingen, Swiss).
4. TALON Resin (#635501 Clontech Laboratories) (3 ml of TALON resin per unit of bed volume) was added to the supernatant (1 L).
5. The resultant was moderately rotated overnight at 4° C.
6. Centrifugation was performed at 4° C. at 700 g for 5 minutes to collect TALON resin.
7. The supernatant was removed.
8. TALON Resin was washed with 40 ml of a washing buffer (50 ml sodium phosphate, 600 mM NaCl).
9. Centrifugation was performed at 4° C. at 700 g for 5 minutes.
10. The supernatant was removed.
11. Steps 8 to 10 above were repeated three times.
12. TALON Resin and a washing buffer (15 ml) were added thereto for resuspension.
13. TALON Resin (3 ml) was transferred therefrom to a gravity flow column.
14. An elution buffer (15 ml) was added to the column for elution of an HIS-tagged protein. Then, a human REIC protein was collected.
15. The eluate was dialyzed using 20 mM Tris-HCl (pH 7.5) and 0.1 M NaCl so that the resultant could be subjected to FPLC (Fast Protein Liquid Chromatography).
16. The human REIC protein was purified by FPLC (Mono Q5/50GL column, GE Healthcare) under the conditions described below.
Buffer
MonoQ buffer A: 20 mm Tris-HCl, pH 7.5, 0.1 M NaCl
MonoQ buffer B: 20 mm Tris-HCl, pH 7.5, 0.5 M NaCl
Flow rate: 1 ml/minute
Flow amount: 70 ml
Fraction size: 1 ml
17. Fractions were analyzed by SDS-PAGE and western blot with the use of an anti-human REIC antibody. The final product was confirmed by SDS-PAGE to have a purity of 95% or greater (FIG. 1).
18. An appropriate fraction was collected.
19. Dialysis was conducted with PBS. The resultant was used or stored as a stock solution.
20. Centriplus YM-50 (#4423, milipore) was used to concentrate the resultant.
21. The protein concentration was determined by Bradford's method.
22. The protein stock solution was preserved at −80° C. before use.

Preparation of Human Monocytes

Human PBMCs (peripheral blood monocytes) were prepared from the blood of healthy donors by a standard method involving Ficoll-Paque centrifugation. The cell collection rate was determined by the trypan blue exclusion method. The survival rate was confirmed to be 99% or greater. For preparation of monocytes, PBMCs were resuspended in LGM-3 (serum-free lymphocyte growth medium-3; Lonza). The cells adhering to a plastic dish (subjected to incubation in a 10-cm dish at 37° C. for 2 hours) were used as monocytes. In some experiments, $CD14^+$ monocytes were separated using $CD14^+$ magnetic-activated cell sorting microbeads (MACS; Milte-nyiBiotec). Purified $CD14^+$ monocytes were resuspended in LGM-3. Using flow cytometry, the purity was always found to exceed 95%.

Treatment of Human Monocytes

PBMCs were cultured alone or in the presence of the recombinant human REIC protein (10 μg/ml) or GM-CSF+IL-4 (2 ng/ml each; R&D Systems). The cells were observed with a phase contrast microscope.

Figure 2:
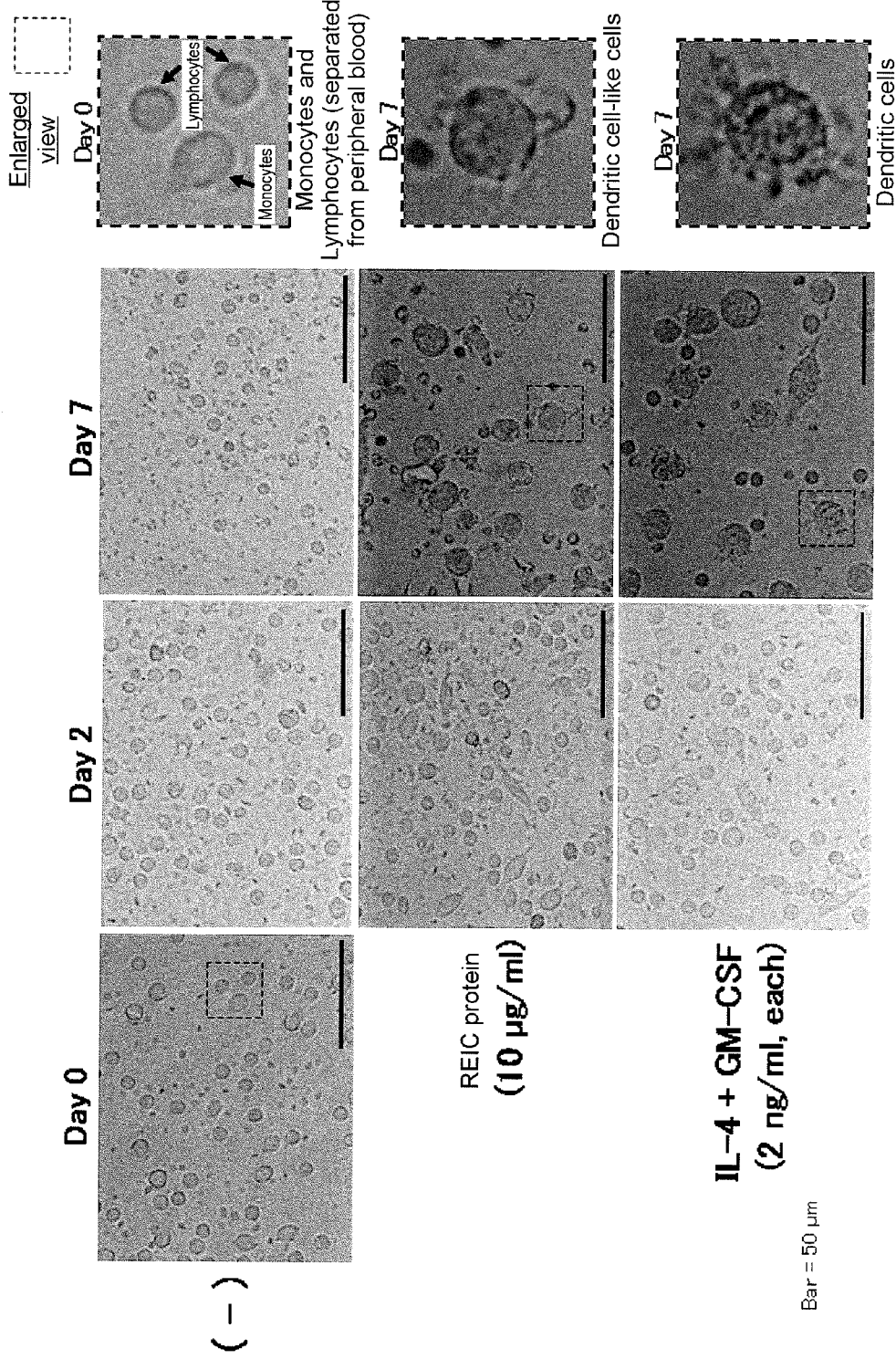
FIG. 2 shows phase contrast microscopic images indicating the induction of dendritic cell-like differentiation from peripheral blood monocytes with the addition of the human REIC protein.

FIG. 2 shows phase contrast microscopic images (for Days 0, 2, and 7) of PBMCs cultured alone or in the presence of the recombinant human REIC protein or GM-CSF+IL-4. In FIG. 2, panels shown on the right side correspond to an enlarged image of a dashed-line rectangle in the image showing protein-free culture (Day 0), that in the image showing culture in the presence of the REIC protein (Day 7), and that in the image showing culture in the presence of GM-CSF+IL-4 (Day 7), respectively. As shown in the figure, in the case in which PBMCs were cultured in the presence of the REIC protein, differentiation into dendritic cell-like cells was observed.

Figure 3:
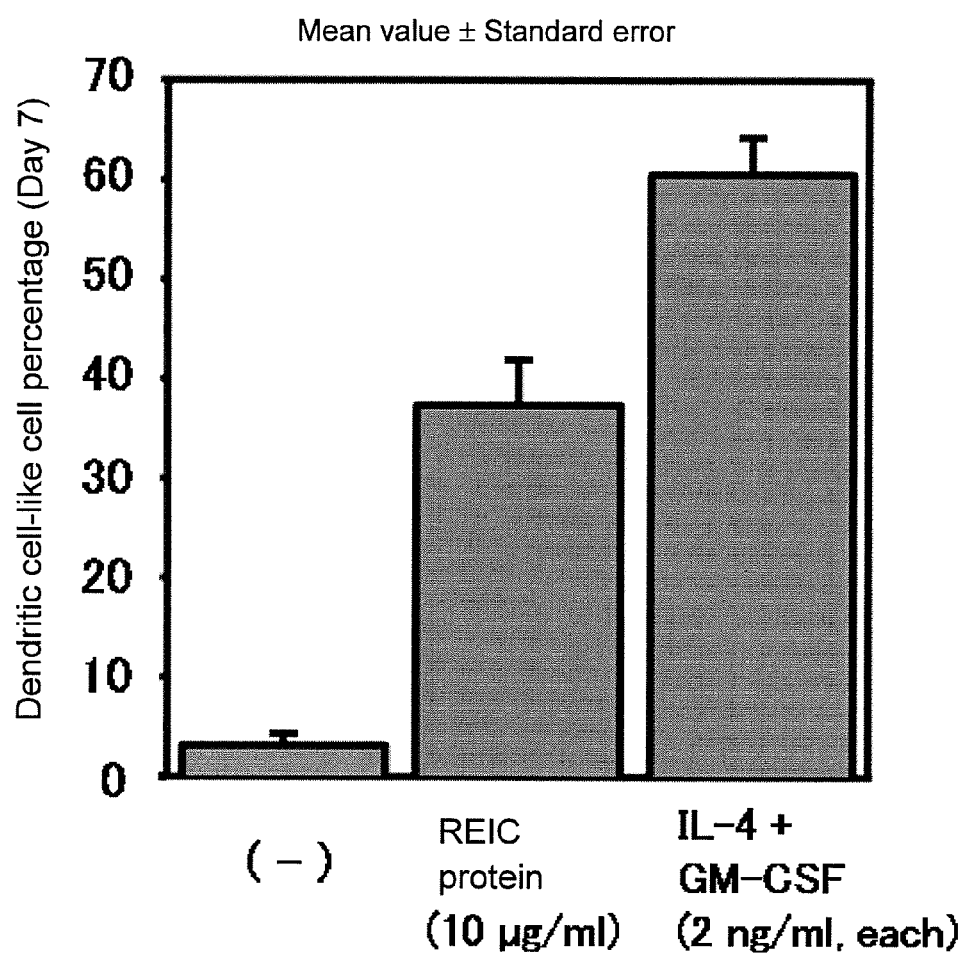
FIG. 3 shows the percentage of all cells represented by dendritic cell-like cells induced to differentiate with the addition of the human REIC protein.

The percentage of all cells represented by dendritic cell-like cells was determined for each culture on Day 7. The percentage of all cells represented by dendritic cell-like cells induced to differentiate with the addition of a human REIC protein was determined as described below. Specifically, in 3 independent experiments, 5 randomly selected visual fields (100 cells each) for each group (the protein-free (−) group, the human REIC protein group, and the IL-4+GM-CSF group) were visually observed and dendritic cell-like cells (which were morphologically large and confirmed to have dendrites) were counted under a microscope on Day 7 after administration. FIG. 3 shows the results. Dendritic cell-like cells accounted for several percent in the case of culture of PBMCs alone. However, the cells accounted for approximately 40% in the case of culture in the presence of the REIC protein, and the cells accounted for approximately 60% in the case of culture in the presence of GM-CSF+IL-4. In addition, dendritic cell-like cells induced by the REIC protein were morphologically similar to dendritic cells induced by GM-CSF+IL-4.

Figure 4:
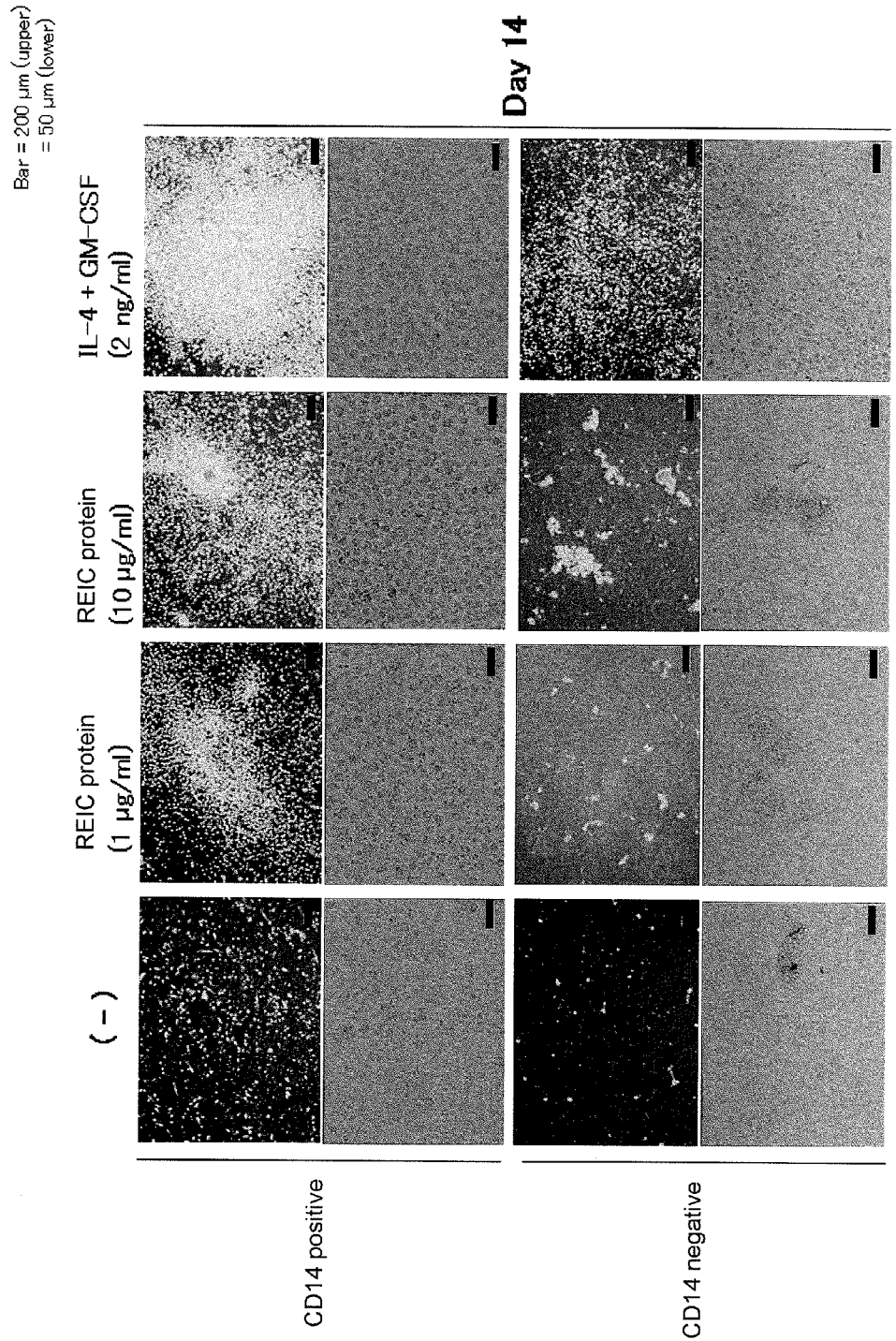
FIG. 4 shows images indicating the induction of dendritic cell-like differentiation from peripheral blood monocytes (CD14 positive cells) with the addition of the human REIC protein.

$CD14^+$ cells and CD14 negative cells were cultured alone or in the presence of the recombinant human REIC protein (1 μg/ml or 10 μg/ml) or GM-CSF+IL-4 (2 ng/ml each). Cells were observed with a phase contrast microscope. Peripheral blood mononuclear cells were composed of monocytes and lymphocytes. In order to determine which cells were induced to differentiate into dendritic cell-like cells, it was attempted to induce dendritic cell-like differentiation from CD14 positive monocytes and from CD14 negative lymphocytes in the presence of commercially available anti-CD14 antibody-conjugated beads with the addition of the human REIC protein. FIG. 4 shows the results of induction of dendritic cell-like differentiation from $CD14^+$ cells. As shown in FIG. 4, the induction of dendritic cell-like differentiation was observed exclusively for the CD14 positive monocytes. As shown in the figure, the number of cells induced to differentiate increased depending on the concentration of the REIC protein added. Accordingly, the human REIC protein was found to have effects of inducing dendritic cell-like differentiation from peripheral blood monocytes (CD14 positive). In addition, the effects were exhibited in a dose-dependent manner.

Western Blot Analysis

PBMCs were treated with the human REIC protein (10 μg/ml) or GM-CSF+IL-4 (2 ng/ml each) and then washed twice with phosphate buffered saline (PBS). The cells were lysed in a cell lysis buffer (50 mM HEPES (pH 7.4), 250 mM NaCl, 1% NP-40, 1 mM DTT, 1 mM PMSF, 5 μg/ml aprotinin, 2 mM Na$_3$VO$_4$, 1 mM NaF, and 10 mM β-GP) for protein extraction, followed by centrifugation. Thereafter, the protein in the supernatant was adjusted to an identical concentration for each experiment. The resultant was diluted with an equivalent amount of a 2×SDS sample buffer and heated at 95° C. for 5 minutes. The sample (protein: 10 μg) was applied to 7.5% SDS-PAGE gel, followed by electroblotting on a polyvinylidine fluorodide (PVDF) membrane. Electroblotting was carried out at room temperature for 1 hour with the use of TBS containing a 10% skimmed milk powder, 6% Glycine, and 0.1% Tween-20. The protein was identified using a 1000-fold diluted rabbit polyclonal anti-human REIC antibody (Abarzua F. et al., Cancer Res. 2005 Nov. 1; 65(21): 9617-22), an anti-phosphorylated Stat1 (Try701) antibody (#9171, Cell Signaling Technology), an anti-phosphorylated Stat3 (Try705) antibody (#9131), and an anti-phosphorylated Stat5 (Try694) antibody (#9351). After sufficient washing with TBS containing 0.1% Tween-20 (T-TBS), the obtained blots were treated with a horseradish peroxidase-bound secondary antibody and sufficiently washed with T-TBS, followed by color development by an enhanced chemiluminescence detection method (ECL kit, Amersham Pharmacia Biotech).

Figure 5:
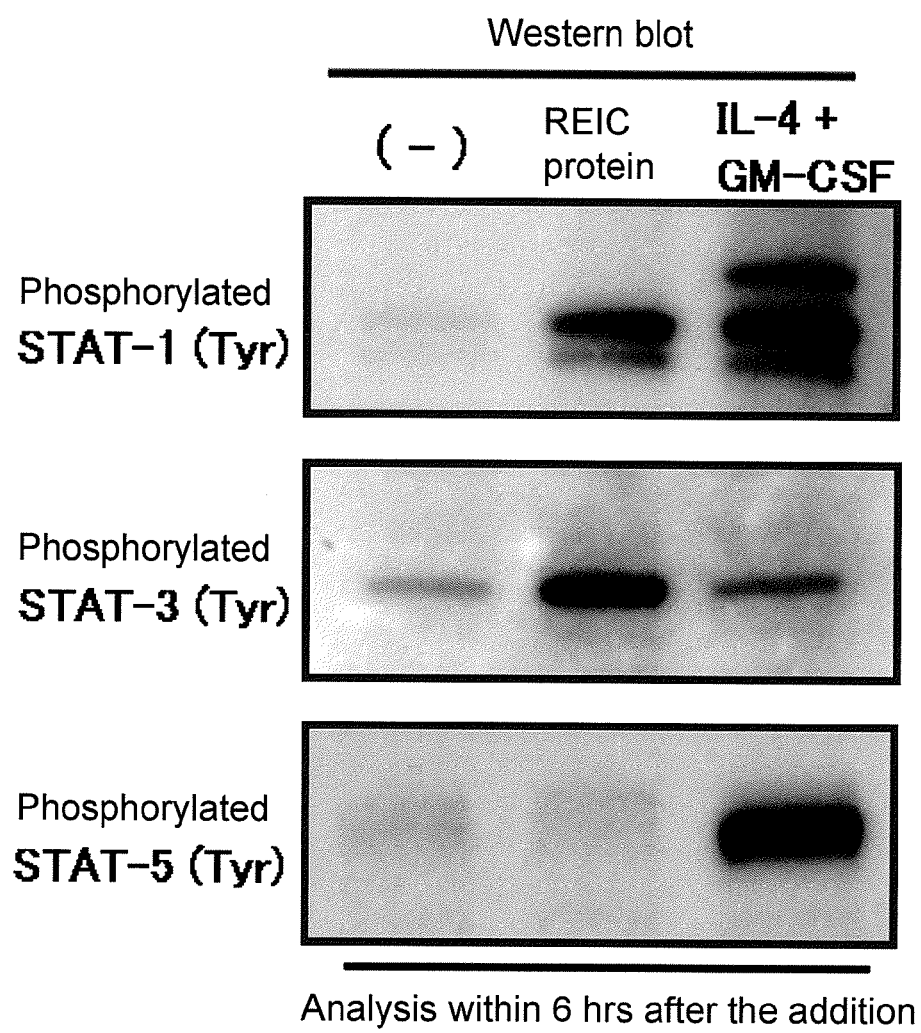
FIG. 5 shows images indicating STAT (signal transducer and activator transcription) activation of peripheral blood monocytes with the addition of the human REIC protein.

FIG. 5 shows results of activation of STAT in peripheral blood mononuclear cells with the addition of the human REIC protein. The increased expression of phosphorylated STAT-1 (Tyr), phosphorylated STAT-3 (Tyr), and phosphorylated STAT-5 (Tyr) indicates activation of these proteins. The activation of such proteins is thought to be important for hemocyte differentiation. That is to say, the findings obtained by the western blot method strongly suggest that the REIC protein has the ability to induce hemocyte differentiation via intracellular STAT signals. In addition, the pattern of the action of the REIC protein upon STAT activation (phosphorylation) differed from that of IL-4+GM-CSF added to positive control dendritic cells. These results and the results obtained by flow cytometry suggest that the addition of the REIC protein causes the induction of dendritic cell-like cells differing from positive control dendritic cells.

Flow Cytometry Analysis

Cell culture was terminated with the addition of cold PBS and then cells were cooled on ice for 10 minutes, followed by incubation. Subsequently, the cells were resuspended using a Pasteur pipette and then recovered. Adhering cells were recovered via trypsin treatment and mixed with floating cells. The cells (approximately 5×10$^5$ cells) were incubated on ice for 60 minutes with the use of PE-conjugated antibodies each diluted 5-fold with PBS (100 μl). The PE-conjugated antibodies used herein were CD11c (12-0116), CD14 (12-0149), CD1a (12-0019), CD40 (12-0409), CD80 (12-0809), CD83 (12-0839), CD86 (12-0869), and HLA-DR (12-9956) (eBioscience). PE-conjugated immunoglobulins G (IgG) (12-4714, 12-4732) with the same isotype were used as negative controls. After incubation, cells were washed once with 1 ml of PBS and resuspended in 500 μl of PBS. Subsequently, 10$^4$ cells were collected using an FACSCalibur flow cytometer (Becton Dickinson), followed by analysis with the use of CellQuest software (Becton Dickinson). An appropriate gate was made based on the forward scatter pattern specific to the cells. Then, only the cells found inside the gate were analyzed. The cells exhibiting a mean fluorescence index (MFI) value greater than that exhibited by control cells incubated with a control antibody of the same isotype were designated as positive cells. Dead cells were removed based on propidium iodide (PI) staining results and/or scatter characteristics. As a result of PI staining, more than 99% of cells were found to have survived.

Endocytosis of FITC-labeled Particles

The above cells were recovered and resuspended at a concentration of 5×10$^6$ cells/ml in cold PBS. FITC-conjugated dextran (50 μg; DX FITC; FD40; Sigma) was added to 0.5 ml of the suspension. Subsequently, the cells were incubated at 4° C. or 37° C. for 1 hour. The cells were washed twice with 1 ml of cold PBS. Then, 10$^4$ cells were obtained using an FACSCalibur flow cytometer and analyzed by CellQuest software.

Figure 6A:
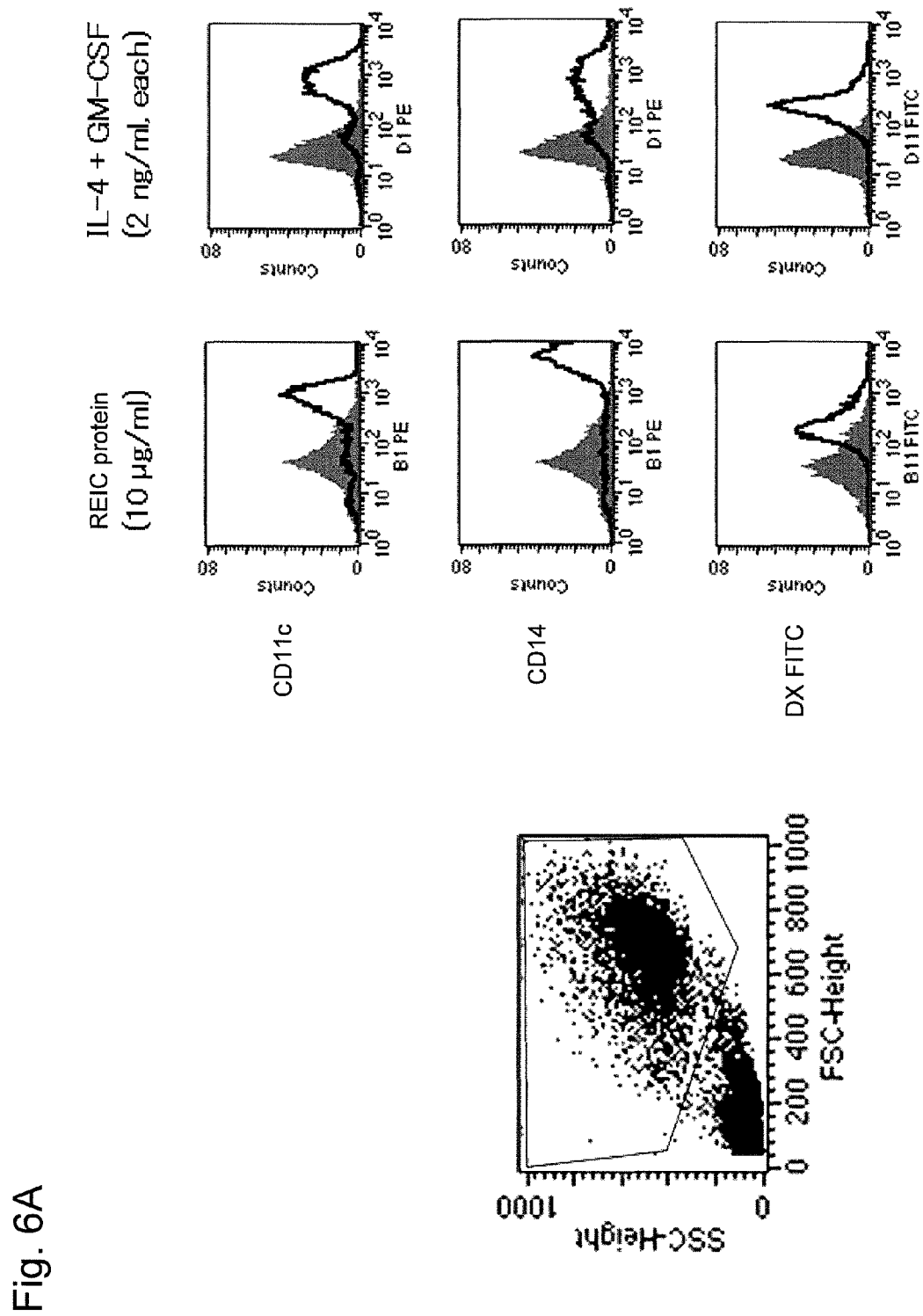
FIG. 6A shows the results of flow cytometry analysis of dendritic cell-like cells induced to differentiate with the addition of the human REIC protein.

FIGS. 6A and 6B show results of flow cytometry analysis of dendritic cell-like cells that were induced to differentiate with the addition of the human REIC protein.

Flow cytometry was performed using cells shown in the enclosed area in FIG. 6A. The enclosed area was established such that it had the following two characteristics: it allowed the removal of debris of cells in a specimen; and it allowed the clear monitoring of dendritic cells in the group treated with IL-4+GM-CSF serving as a positive control.

In the chart on the right side in FIG. 6A, "CD11c" refers to a bone marrow-derived leukocyte marker (a non-lymphocyte marker). In addition, "CD14" refers to a monocyte or macrophage marker. Further, "DX FITC" refers to FITC-tagged dextran; this substance is often used for evaluation of the phagocytotic (endocytotic) capacity of leukocyte-derived cells.

Therefore, cells that were induced to differentiate with the addition of the REIC protein are more similar to monocyte-derived cells than bone marrow leukocyte-derived dendritic cells induced with the addition of IL-4+GM-CSF. In addition, the cells are dendritic cell-like cells having the ability to phagocytize a foreign body/antibody substantially comparable to that of dendritic cells.

In addition, in FIG. 6B, "CD1a" refers to a dendritic cell marker that is thought to be involved in the presentation of a non-peptidic antigen (e.g., lipid antigen). Further, "CD40" refers to a dendritic cell marker that is a receptor of the CD40 ligand (having an ability to induce dendritic cells even when used alone). "CD80" refers to a dendritic cell marker and is thought to be involved together with CD86 in the presentation of antigens to T lymphocytes. "CD83" refers to a dendritic cell marker and is used as a mature dendritic cell marker. "CD86" refers to a dendritic cell marker and is used as an immature dendritic cell marker. "HLA-DR" refers a dendritic cell marker and is strongly expressed during dendritic cell differentiation.

Accordingly, cells that were induced to differentiate with the addition of the REIC protein showed a marker expression pattern similar (but not identical) to that of dendritic cells that were induced with the addition of IL-4+GM-CSF.

In conclusion, in view of the other in vitro experimental results, in addition to the above results, it was found that the addition of the REIC protein results in the induction of differentiation of dendritic cell-like cells from CD14-positive peripheral blood monocytes. The cells are morphologically different from peripheral blood monocytes. Also, they are different from dendritic cells that were induced with the addition of IL-4+GM-CSF.

The results shown in FIG. 6 indicate that anticancer immunity can be activated by causing dendritic-like cells induced by the human REIC protein and the REIC protein (as in the case of treatment with IL-4+GM-CSF or IL-4+GM-CSFDC) to have improved in vivo antigen phagocytosis/antibody presentation capacity.

Figure 7:
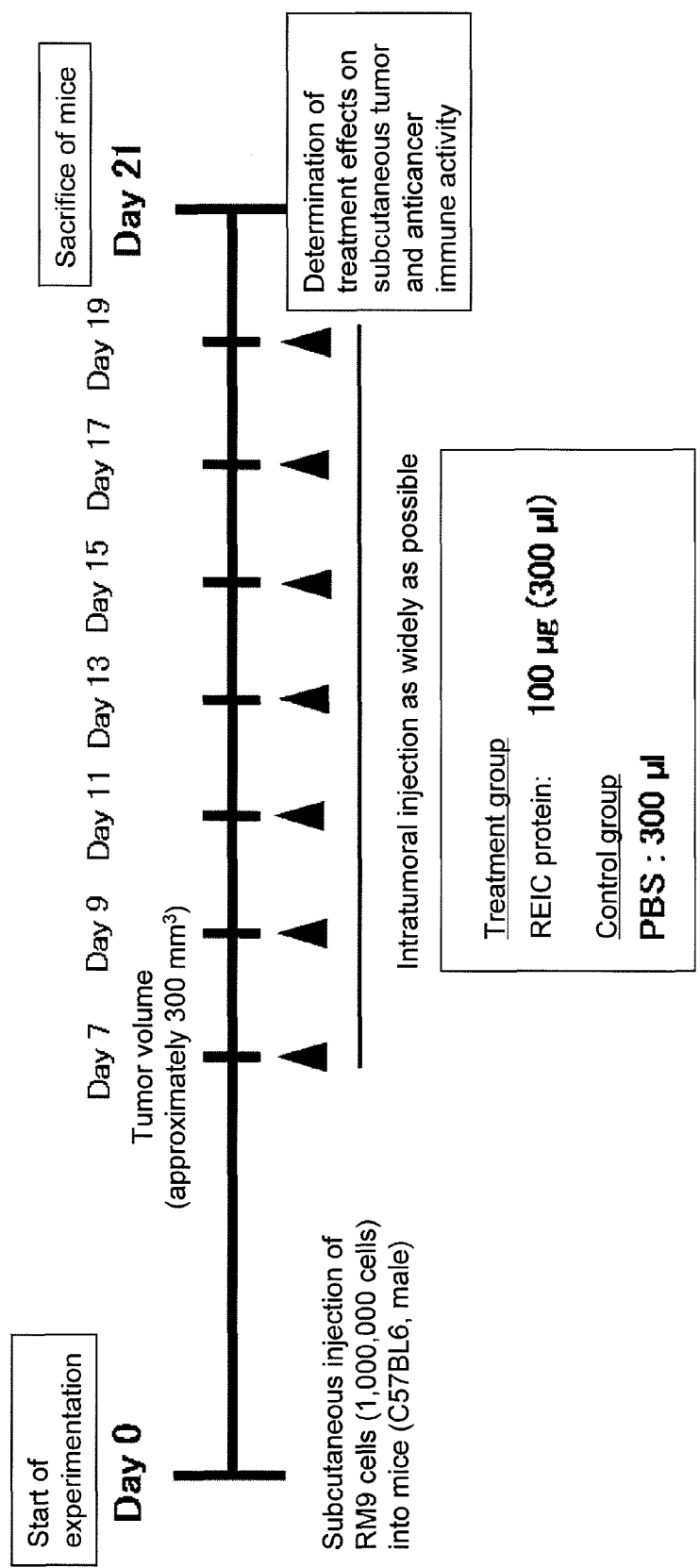
FIG. 7 shows experimental protocols of intratumoral administration of the human REIC protein.

Determination of Tumor-suppressive Effects of the REIC Protein in In vivo Experiments RM9 cells (1×10$^6$ cells) were subcutaneously injected into mice (C57BL6, male). On Days 7, 9, 11, 13, 15, 17, and 19 after injection (provided that Day 7 was designated to be the day of the start of administration of the REIC protein), the REIC protein (100 μg (300 μl)) or PBS (300 μl) used as a control was uniformly injected into each tumor formed from the cells. On Day 21, mice were sacrificed. Therapeutic effects upon subcutaneous tumors were examined, and anticancer immune activity was determined. FIG. 7 shows in vivo experimental protocols. Tumor size was measured several days after the above operation. Tumor volume was obtained by the following formula: $\frac{1}{2}\times$(minimum diameter)$^2\times$(maximum diameter).

Figure 8A:
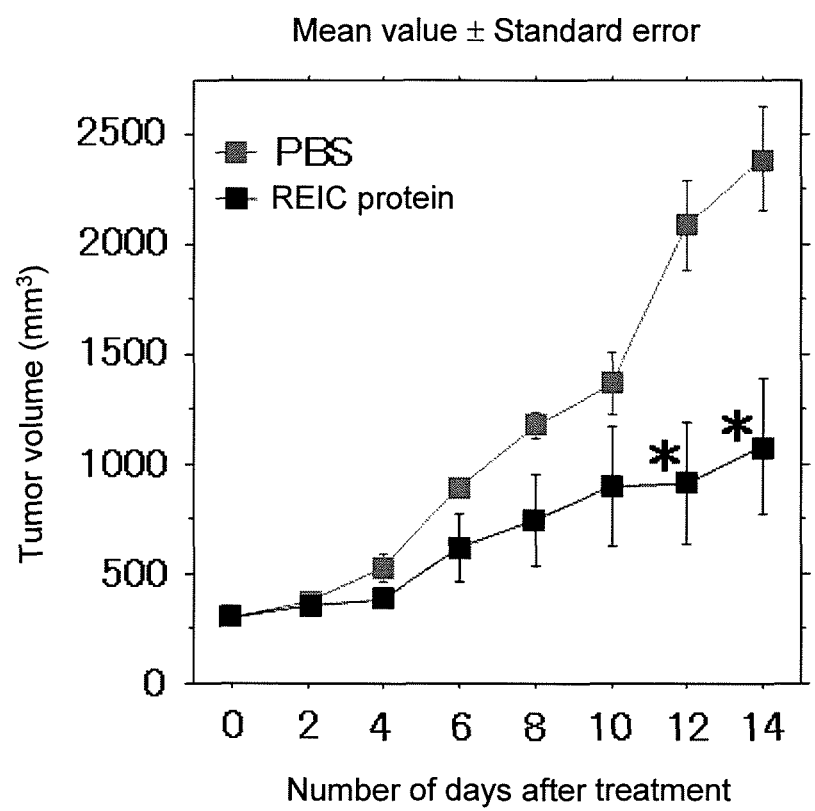
FIG. 8A shows tumor growth inhibitory effects (time-dependent changes in tumor volume) observed after intratumoral administration of the human REIC protein.
Figure 8B:
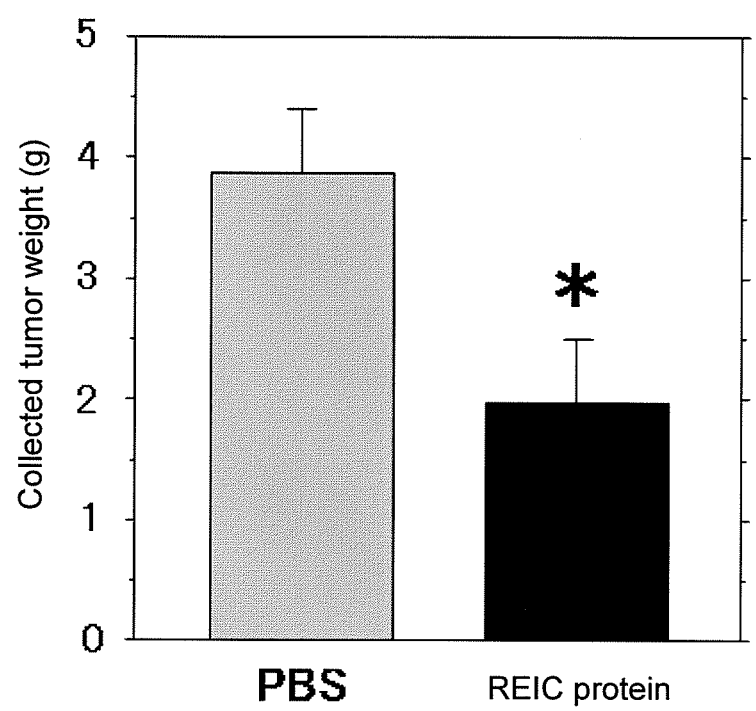
FIG. 8B shows tumor growth inhibitory effects (based on tumor weight) observed after intratumoral administration of the human REIC protein.
Figure 8C:
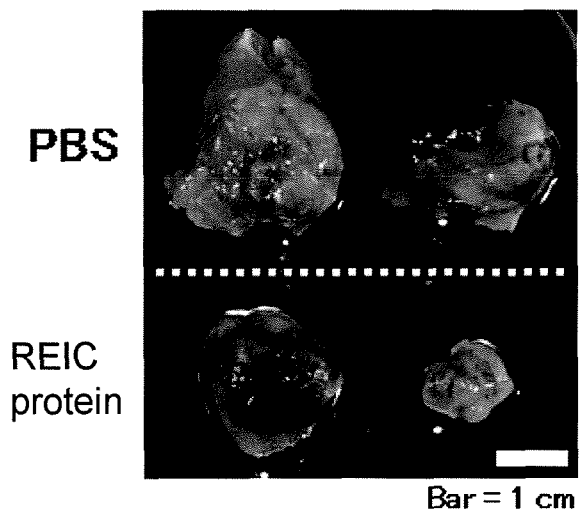
FIG. 8C shows tumor growth inhibitory effects (shown in tumor image) observed after intratumoral administration of the human REIC protein.

FIG. 8A shows time-dependent changes in tumor volume after treatment. In addition, FIG. 8B shows the volume of tumors collected from the mice. Further, FIG. 8C shows an image of a tumor collected from a mouse. As shown in FIGS. 8A to 8C, it was possible to suppress tumor growth via administration of the human REIC protein. Determination of effects of increasing anticancer immune activity of the REIC protein via in vitro cytolytic assay Splenocytes were collected from mice or control mice treated by the method shown in FIG. 7 (on Day 14 after the start of administration of the REIC protein). The splenocytes were used as effectors and cultured with RM9 cells (target cells) on a round-bottom 96-well plate. The effector/target ratio (E/T ratio) was 100:1, 50:1, 25:1, or 12.5:1. Target cells were added to wells ($5\times10^3$ cells each). The supernatant was collected. Lactate dehydrogenase released from lysed RM9 cells was examined by nonradioactive cytotoxicity assay (CytoTox96, Promega). The lysed cell percentage was calculated by the following formula.

(Release during experimentation−Spontaneous release from effectors)/(Maximum release of targets−Spontaneous release of targets)×100(%)

Figure 9:
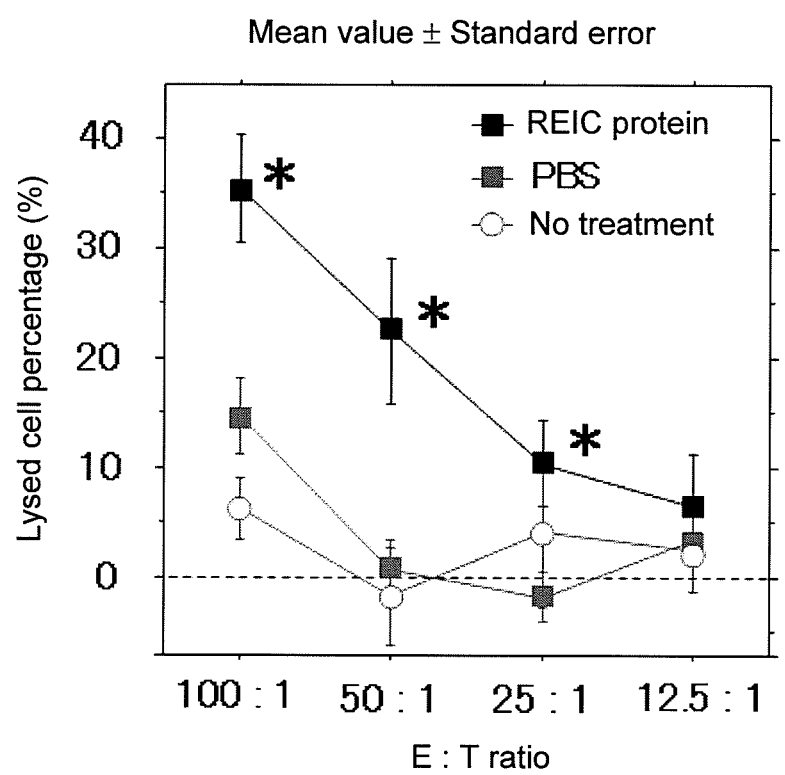
FIG. 9 shows elevation of anticancer immune activity as a result of intratumoral administration of the human REIC protein.

FIG. 9 shows the results of analysis of anticancer cell immune activity of mouse splenocytes upon RM9 cells. As shown in FIG. 9, when the REIC protein was administered, the percentage of lysed cells increased depending on the effector/target ratio. Accordingly, it was revealed that the REIC protein has an effect of increasing anticancer cell immune activity.

In this Example, data are represented by the mean±SEM. An unpaired Student's t-test was used for statistical analysis involving 2 groups. Statistical significance was assumed when the p value was <0.05.

Figure 10:
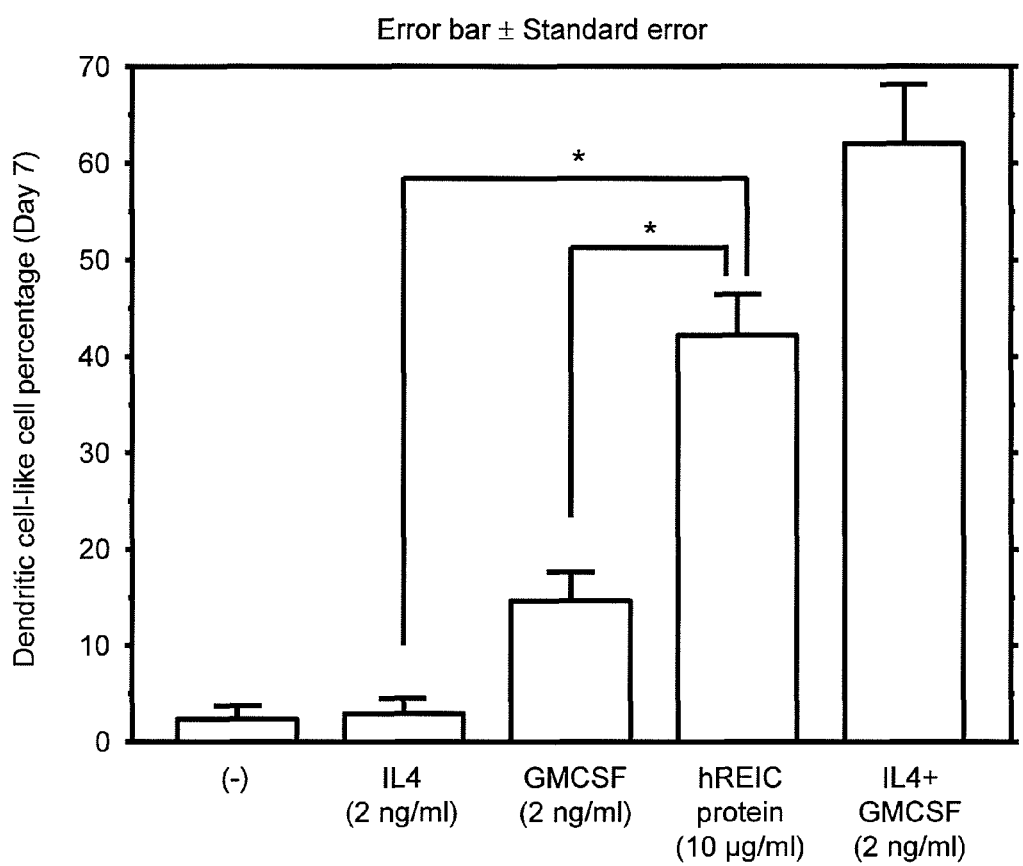
FIG. 10 shows the induction of dendritic cell-like differentiation from peripheral blood mononuclear cells with the addition of the human REIC protein.

Induction of Dendritic Cell-like Differentiation from Peripheral Blood Mononuclear Cells with the Addition of the Human REIC Protein Comparison among a group treated with the REIC protein, a group treated with IL-4 alone, a group treated with GM-CSF alone, and a group treated with IL-4+GM-CSF was carried out in terms of the percentage of all cells represented by dendritic cell-like cells induced to differentiate. In FIG. 10, the vertical axis represents the percentage of cells with dendritic cell-like features (the percentage of all cells represented by dendritic cell-like cells that were morphologically large and confirmed to have dendrites). The cells were visually counted at random with a microscope on Day 7 after the addition of the relevant substance.

As shown in FIG. 10, the degree of induction of differentiation into dendritic cell-like cells in the group treated with the human REIC protein was statistically significantly greater (shown with "*") than that in the group treated with IL-4 alone and that in the group treated with GM-CSF alone.

Accordingly, the ability of the human REIC protein to induce human peripheral blood monocytes to differentiate into dendritic cell-like cells at the concentrations shown in FIG. 10 is significantly greater than that in a group treated with IL-4 or GM-CSF (known as a cytokine) alone. Specifically, the human REIC protein is superior to cytokines such as IL-4 and GM-CSF in terms of induction of differentiation into dendritic cell-like cells and has greater usefulness than such cytokines.

Figure 11:
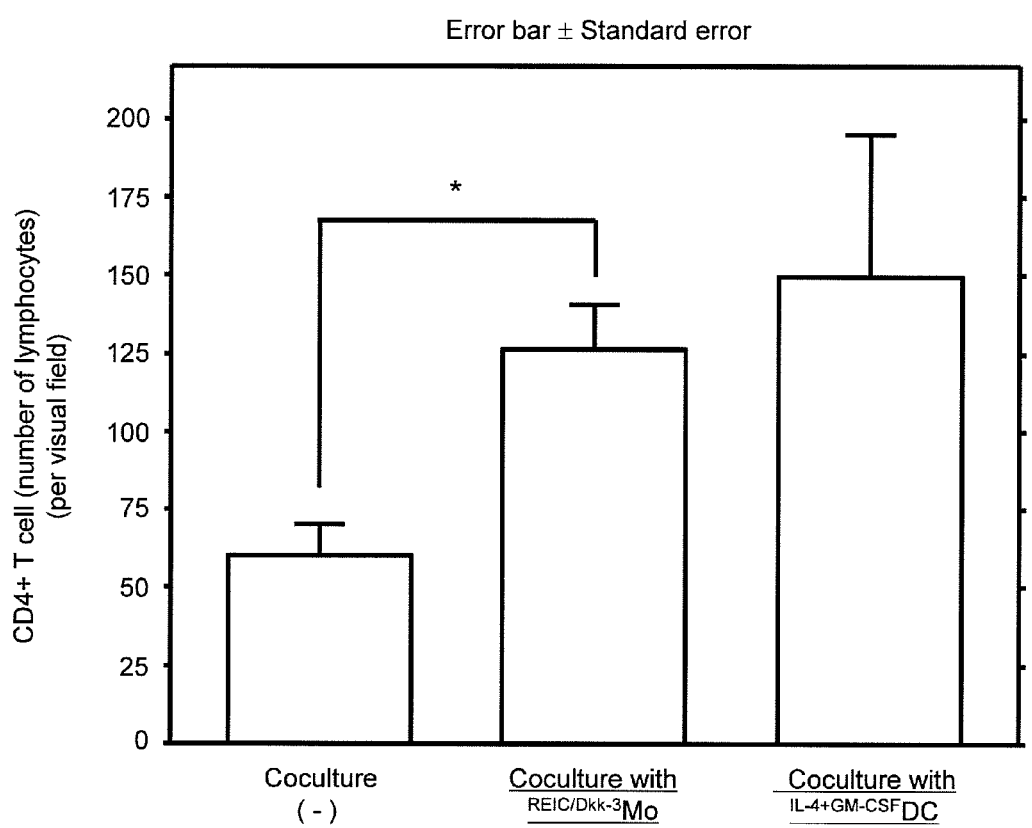
FIG. 11 shows the activity of inducing an allo (allogenic) reaction with the use of $CD4^+$ T cells (lymphocytes) in dendritic-like cells induced with the addition of the human REIC protein

Activity of Inducing an Allo (Allogenic) Reaction with the Use of CD4$^+$ T Cells (Lymphocytes) in Dendritic-like Cells Induced with the Addition of the Human REIC Protein In order to evaluate an anticancer immunity function of REIC protein-induced dendritic-like cells, evaluation of activity of inducing an allo (allogenic) reaction with the use of CD4$^+$ T cells (lymphocytes) was conducted. On Day 0, CD14$^+$ monocytes were collected from peripheral blood mononuclear cells with the use of MicroBeads (Miltenyi Biotec) for collection of CD14$^+$ monocytes. The human REIC protein and IL-4+GM-CSF were separately added thereto. On Day 7, the different cells were collected and designated as REIC protein-induced dendritic-like cells and IL-4+GM-CSF-induced dendritic cells (positive control), respectively. In addition, on Day 7, CD4$^+$ T cells were selected and collected from peripheral blood mononuclear cells of a donor whose HLA-DR differed from that of a donor of dendritic cells with the use of MicroBeads (Miltenyi Biotec) used for collection of CD4$^+$ T cells. A chemical substance (CFSE), which emits fluorescence, was added to the CD4$^+$ T cells at a concentration of 0.05 μm, followed by culture at room temperature for 5 minutes for cell labeling. Labeled cells were used as allo naive CD4$^+$ T cells. Similarly, on Day 7, CD4$^+$ T cells ($1\times10^5$ cells) were cocultured on a round bottom 96-well plate with the REIC protein-induced dendritic-like cells ($6.25\times10^3$ cells per well) or the IL-4+GM-CSF-induced dendritic cells ($6.25\times10^3$ cells per well) for a positive control. CFSE-labeled CD4$^+$ T cells were cultured alone for a negative control. Coculture was carried out for 4 days in an incubator under culture conditions of 37° C. in the presence of 5% CO$_2$ and 95% air. On Day 11, the number of CFSE-positive lymphocytes in a random visual field was determined under a microscope. FIG. 11 shows the results.

FIG. 11 shows that REIC protein-induced dendritic-like cells (REIC/Dkk-3Mo) have the ability to cause CD4$^+$ T cells to grow via coculture, with the increase in the number of cells being statistically more significant (represented by "*") than that in the case of the control group. In addition, it has been demonstrated that such ability is statistically comparable to that of IL-4+GM-CSF-induced dendritic cells used for a positive control. Specifically, in this Example, dendritic-like cells induced by the human REIC protein and the REIC protein can serve as a very useful means for improving anticancer immunity and treating cancer in clinical practice, as in the case of treatment with IL-4+GM-CSF or IL-4+GM-CSFDC.

Industrial Applicability

The REIC protein has been found to have the following effects when compared with IL-2 and a group of many cytokines conventionally known to have immune activation effects.
(1) The REIC protein causes anticancer immune activation and thus exhibits antitumor effects even when used alone.
(2) The REIC protein itself is characterized in that REIC gene expression is absent/reduced in many types of cancer and therefore REIC protein formulations are effective for a wide range of cancers.
(3) The REIC protein causes anticancer immune activation and thus it can be expected to have the effect of improving not only a localized cancer lesion treated therewith but also a cancer metastatic lesion, and to have the effect of preventing cancer (metastasis).

(4) Simultaneous administration of the agent of the present invention and a different existing cancer antigen protein can cause systematic anticancer immune activation via the induction of differentiation into dendritic(-like) cells, allowing prevention of carcinogenesis itself.

The REIC protein can be used as a cancer immunotherapeutic agent.

All publications, patents, and patent applications cited herein are incorporated herein by reference in their entirety.

The invention claimed is:

1. A method for inducing differentiation from monocytes into dendritic cell-like cells in vitro, which comprises contacting the monocytes with an agent for inducing differentiation from monocytes into dendritic cell-like cells comprising the following REIC protein:
   a protein consisting of the amino acid sequence shown in SEQ ID NO: 2.

2. The method for inducing differentiation from monocytes into dendritic cell-like cells according to claim 1, wherein the monocytes are peripheral blood monocytes.

3. A method for inducing CD14 positive monocytes to differentiate into dendritic cell-like cells, which comprises culturing monocytes collected from an animal in vitro in the presence of the following REIC protein:
   a protein consisting of the amino acid sequence shown in SEQ ID NO: 2.

4. The method according to claim 3, wherein the monocytes are peripheral blood monocytes.

* * * * *

SEQUENCE LISTING

<160> NUMBER OF SEQ ID NOS: 2

<210> SEQ ID NO 1
<211> LENGTH: 1053
<212> TYPE: DNA
<213> ORGANISM: Homo sapiens
<220> FEATURE:
<221> NAME/KEY: CDS
<222> LOCATION: (1)..(1053)

<400> SEQUENCE: 1

```
atg cag cgg ctt ggg gcc acc ctg ctg tgc ctg cta ctg gcg gcg gcg      48
Met Gln Arg Leu Gly Ala Thr Leu Leu Cys Leu Leu Leu Ala Ala Ala
1               5                   10                  15 gtc ccc acg gcc ccc gcg ccc gct ccg acg gcg acc tcg gct cca gtc      96
Val Pro Thr Ala Pro Ala Pro Ala Pro Thr Ala Thr Ser Ala Pro Val
                20                  25                  30 aag ccc ggc ccg gct ctc agc tac ccg cag gag gag gcc acc ctc aat     144
Lys Pro Gly Pro Ala Leu Ser Tyr Pro Gln Glu Glu Ala Thr Leu Asn
            35                  40                  45 gag atg ttc cgc gag gtt gag gaa ctg gtg gag gac acg cag cac aaa     192
Glu Met Phe Arg Glu Val Glu Glu Leu Val Glu Asp Thr Gln His Lys
        50                  55                  60 ttg cgc agc gcg gtg gaa gag atg gag gca gaa gaa gct gct gct aaa     240
Leu Arg Ser Ala Val Glu Glu Met Glu Ala Glu Glu Ala Ala Ala Lys
65                  70                  75                  80 gca tca tca gaa gtg aac ctg gca aac tta cct ccc agc tat cac aat     288
Ala Ser Ser Glu Val Asn Leu Ala Asn Leu Pro Pro Ser Tyr His Asn
                85                  90                  95 gag acc aac aca gac acg aag gtt gga aat aat acc atc cat gtg cac     336
Glu Thr Asn Thr Asp Thr Lys Val Gly Asn Asn Thr Ile His Val His
                100                 105                 110 cga gaa att cac aag ata acc aac aac cag gct cga caa atg gtc ttt     384
Arg Glu Ile His Lys Ile Thr Asn Asn Gln Ala Arg Gln Met Val Phe
            115                 120                 125 tca gag aca gtt atc aca tct gtg gga gac gaa gaa ggc aga agg agc     432
Ser Glu Thr Val Ile Thr Ser Val Gly Asp Glu Glu Gly Arg Arg Ser
        130                 135                 140 cac gag tgc atc atc gac gag gac tgt ggg ccc agc atg tac tgc cag     480
His Glu Cys Ile Ile Asp Glu Asp Cys Gly Pro Ser Met Tyr Cys Gln
145                 150                 155                 160 ttt gcc agc ttc cag tac acc tgc cag cca tgc cgg ggc cag agg atg     528
Phe Ala Ser Phe Gln Tyr Thr Cys Gln Pro Cys Arg Gly Gln Arg Met
                165                 170                 175 ctc tgc acc cgg gac agt gag tgc tgt gga gac cag ctg tgt gtc tgg     576
Leu Cys Thr Arg Asp Ser Glu Cys Cys Gly Asp Gln Leu Cys Val Trp
            180                 185                 190 ggt cac tgc acc aaa atg gcc acc agg ggc agc aat ggg acc atc tgt     624
Gly His Cys Thr Lys Met Ala Thr Arg Gly Ser Asn Gly Thr Ile Cys
        195                 200                 205 gac aac cag agg gac tgc cag ccg ggg ctg tgt tgt gcc ttc cag aga     672
Asp Asn Gln Arg Asp Cys Gln Pro Gly Leu Cys Cys Ala Phe Gln Arg
    210                 215                 220 ggc ctg ctg ttc cct gtg tgc ata ccc ctg ccc gtg gag ggc gag ctt     720
Gly Leu Leu Phe Pro Val Cys Ile Pro Leu Pro Val Glu Gly Glu Leu
```

```
                   225                 230                 235                 240
tgc cat gac ccc gcc agc cgg ctt ctg gac ctc atc acc tgg gag cta       768
Cys His Asp Pro Ala Ser Arg Leu Leu Asp Leu Ile Thr Trp Glu Leu
                    245                 250                 255 gag cct gat gga gcc ttg gac cga tgc cct tgt gcc agt ggc ctc ctc       816
Glu Pro Asp Gly Ala Leu Asp Arg Cys Pro Cys Ala Ser Gly Leu Leu
                260                 265                 270 tgc cag ccc cac agc cac agc ctg gtg tat gtg tgc aag ccg acc ttc       864
Cys Gln Pro His Ser His Ser Leu Val Tyr Val Cys Lys Pro Thr Phe
            275                 280                 285 gtg ggg agc cgt gac caa gat ggg gag atc ctg ctg ccc aga gag gtc       912
Val Gly Ser Arg Asp Gln Asp Gly Glu Ile Leu Leu Pro Arg Glu Val
        290                 295                 300 ccc gat gag tat gaa gtt ggc agc ttc atg gag gag gtg cgc cag gag       960
Pro Asp Glu Tyr Glu Val Gly Ser Phe Met Glu Glu Val Arg Gln Glu
305                 310                 315                 320 ctg gag gac ctg gag agg agc ctg act gaa gag atg gcg ctg ggg gag      1008
Leu Glu Asp Leu Glu Arg Ser Leu Thr Glu Glu Met Ala Leu Gly Glu
                325                 330                 335 cct gcg gct gcc gcc gct gca ctg ctg gga ggg gaa gag att tag          1053
Pro Ala Ala Ala Ala Ala Leu Leu Gly Gly Glu Glu Ile
            340                 345                 350

<210> SEQ ID NO 2
<211> LENGTH: 350
<212> TYPE: PRT
<213> ORGANISM: Homo sapiens

<400> SEQUENCE: 2

Met Gln Arg Leu Gly Ala Thr Leu Leu Cys Leu Leu Leu Ala Ala
1               5                   10                  15

Val Pro Thr Ala Pro Ala Pro Ala Pro Thr Ala Thr Ser Ala Pro Val
                20                  25                  30

Lys Pro Gly Pro Ala Leu Ser Tyr Pro Gln Glu Glu Ala Thr Leu Asn
            35                  40                  45

Glu Met Phe Arg Glu Val Glu Glu Leu Val Glu Asp Thr Gln His Lys
50                  55                  60

Leu Arg Ser Ala Val Glu Glu Met Glu Ala Glu Glu Ala Ala Ala Lys
65                  70                  75                  80

Ala Ser Ser Glu Val Asn Leu Ala Asn Leu Pro Pro Ser Tyr His Asn
                85                  90                  95

Glu Thr Asn Thr Asp Thr Lys Val Gly Asn Asn Thr Ile His Val His
            100                 105                 110

Arg Glu Ile His Lys Ile Thr Asn Asn Gln Ala Arg Gln Met Val Phe
        115                 120                 125

Ser Glu Thr Val Ile Thr Ser Val Gly Asp Glu Glu Gly Arg Arg Ser
    130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190

Gly His Cys Thr Lys Met Ala Thr Arg Gly Ser Asn Gly Thr Ile Cys
        195                 200                 205

Asp Asn Gln Arg Asp Cys Gln Pro Gly Leu Cys Cys Ala Phe Gln Arg
    210                 215                 220
```

-continued

```
Gly Leu Leu Phe Pro Val Cys Ile Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
            260                 265                 270

Cys Gln Pro His Ser His Ser Leu Val Tyr Val Cys Lys Pro Thr Phe
        275                 280                 285

Val Gly Ser Arg Asp Gln Asp Gly Glu Ile Leu Leu Pro Arg Glu Val
    290                 295                 300

Pro Asp Glu Tyr Glu Val Gly Ser Phe Met Glu Glu Val Arg Gln Glu
305                 310                 315                 320

Leu Glu Asp Leu Glu Arg Ser Leu Thr Glu Glu Met Ala Leu Gly Glu
            325                 330                 335

Pro Ala Ala Ala Ala Ala Ala Leu Leu Gly Gly Glu Glu Ile
                340                 345                 350
```